United States Patent
Furuta et al.

(10) Patent No.: US 11,940,405 B2
(45) Date of Patent: Mar. 26, 2024

(54) SENSOR ELEMENT, GAS SENSOR, AND METHOD FOR MANUFACTURING SENSOR ELEMENT

(71) Applicant: NGK SPARK PLUG CO., LTD., Nagoya (JP)

(72) Inventors: Hitoshi Furuta, Nagoya (JP); Akinori Kojima, Nagoya (JP)

(73) Assignee: NITERRA CO., LTD., Nagoya (JP)

( * ) Notice: Subject to any disclaimer, the term of this patent is extended or adjusted under 35 U.S.C. 154(b) by 413 days.

(21) Appl. No.: 17/004,603

(22) Filed: Aug. 27, 2020

(65) Prior Publication Data

US 2021/0080423 A1 Mar. 18, 2021

(30) Foreign Application Priority Data

Sep. 18, 2019 (JP) ................................. 2019-169124
Mar. 4, 2020 (JP) ................................. 2020-036511

(51) Int. Cl.
*G01N 27/407* (2006.01)
*B32B 18/00* (2006.01)
*C04B 37/00* (2006.01)
*G01N 33/00* (2006.01)

(52) U.S. Cl.
CPC ......... *G01N 27/4071* (2013.01); *B32B 18/00* (2013.01); *C04B 37/003* (2013.01);
(Continued)

(58) Field of Classification Search
CPC ........... G01N 27/4071; G01N 27/4074; G01N 33/0037; G01N 27/417; G01N 27/4077;
(Continued)

(56) References Cited

U.S. PATENT DOCUMENTS

| | | | | |
|---|---|---|---|---|
| 6,537,431 B1* | 3/2003 | Tatsumoto | ......... | G01N 27/4071 204/426 |
| 2007/0214865 A1* | 9/2007 | Nakae | ................. | C04B 37/005 73/19.01 |

(Continued)

FOREIGN PATENT DOCUMENTS

| | | | |
|---|---|---|---|
| JP | 2013117428 A | * 6/2013 | |
| JP | 2019-002739 A | 1/2019 | |
| WO | WO-2018016604 A1 | * 1/2018 | ......... G01N 27/4072 |

OTHER PUBLICATIONS

Furuta et al., English translation of JP-2013117428-A, 2013 (Year: 2013).*

*Primary Examiner* — Joshua L Allen
*Assistant Examiner* — Shizhi Qian
(74) *Attorney, Agent, or Firm* — Sughrue Mion, PLLC

(57) ABSTRACT

A sensor element (10) having a laminate structure, and extending in an axial direction AX, the sensor element including a first and second ceramic layers (118B, 115) disposed apart from each other in a laminating direction; a third ceramic layer (118) intervening between the first and second ceramic layers in the laminating direction and having a hollow space (10G) formed therein; and an internal space which is the hollow space surrounded by the first ceramic layer, the second ceramic layer, and the third ceramic layer, wherein, at a periphery (10f) of the internal space, a fourth ceramic layer (181) containing as a main component a ceramic material different from that contained as a main component in the first and third ceramic layers intervenes between the first ceramic layer and the third ceramic layer which are exposed to the internal space. Also disclosed is a method for manufacturing the gas sensor element.

16 Claims, 6 Drawing Sheets

(52) U.S. Cl.
CPC ..... *G01N 27/4074* (2013.01); *G01N 33/0037* (2013.01); *B32B 2315/02* (2013.01); *B32B 2457/00* (2013.01); *C04B 2237/064* (2013.01); *C04B 2237/068* (2013.01); *C04B 2237/343* (2013.01); *C04B 2237/561* (2013.01); *C04B 2237/595* (2013.01)

(58) Field of Classification Search
CPC ...... G01N 27/409; G01N 27/41; B32B 18/00; B32B 2315/02; B32B 2457/00; C04B 37/003; C04B 2237/064; C04B 2237/068; C04B 2237/343; C04B 2237/561; C04B 2237/595; C04B 2235/6028; C04B 2237/348; C04B 2237/66; Y02A 50/20
See application file for complete search history.

(56) References Cited

U.S. PATENT DOCUMENTS

| | | | | |
|---|---|---|---|---|
| 2013/0104625 | A1* | 5/2013 | Otsuka | G01N 33/0037 73/23.31 |
| 2013/0260983 | A1* | 10/2013 | Omori | C04B 35/63456 501/134 |
| 2015/0253281 | A1* | 9/2015 | Saito | G01N 27/4071 204/416 |
| 2015/0276657 | A1* | 10/2015 | Sekiya | G01N 27/4072 204/424 |
| 2019/0145925 | A1* | 5/2019 | Fujii | G01N 27/4062 204/424 |

\* cited by examiner

SENSOR ELEMENT, GAS SENSOR, AND METHOD FOR MANUFACTURING SENSOR ELEMENT

BACKGROUND OF THE INVENTION

1. Field of the Invention

The present invention relates to a sensor element adapted for detecting the concentration of a particular gas contained in, for example, combustion gas or exhaust gas of a combustor, an internal combustion engine, etc., to a gas sensor having the sensor element, and to a method for manufacturing the sensor element.

2. Description of the Related Art

Conventionally, a gas sensor is used for detecting the concentration of a particular component (oxygen, etc.) in exhaust gas of an internal combustion engine. The gas sensor internally has a sensor element. According to a known structure of the sensor element, the sensor element has a plate shape in which a plurality of ceramic layers are laminated, and has a solid electrolyte body and a pair of electrodes disposed on the solid electrolyte body. One of the two electrodes faces an air (atmosphere) introduction hole which opens toward the interior of the sensor element (see Patent Document 1).

As shown in FIG. 8, this atmosphere introduction hole 510 opens at a rear end surface of the sensor element. The atmosphere introduction hole 510 is formed as follows. A third layer 503 having, for example, a rectangular hollow space that opens at a rear end thereof as viewed in the direction of lamination is disposed between a first layer 501 and a second layer 502, which have the same dimensions as those of the sensor element as viewed in the laminating direction.

[Patent Document 1] Japanese Patent Application Laid-Open (kokai) No. 2019-2739

Problems to be Solved by the Invention

However, in some cases, a crack K develops outward from the atmosphere introduction hole 510, particularly in a width direction of the sensor element between the first layer 501 and the third layer 503 and between the second layer 502 and the third layer 503.

If the crack K develops so as to reach the outside from the atmosphere introduction hole 510, the atmosphere introduction hole 510 fails to function as expected. Even in the case of a small crack K, the crack K may progress to the outside as a result of imparting thermal shock such as multiple heat cycles on the sensor element.

Conceivably, such a crack K develops for the following reason. As shown in FIG. 9, in forming the atmosphere introduction hole 510, after a paste 505 that contains burning-off carbon is charged into the hollow space of a third-layer green sheet 503G which is to become the atmosphere introduction hole 510, a first-layer green sheet 501G is laminated on the third-layer green sheet 503G; then, the resultant laminate is fired to burn off the paste 505, thereby forming the atmosphere introduction hole 510. The use of the paste 505 prevents defective formation of the atmosphere introduction hole 510, which would otherwise result from imparting a load between the first-layer green sheet 501G and the second-layer green sheet 502G with resultant deformation of the hollow space of the third-layer green sheet 503G.

In firing, the first-layer green sheet 501G and the second-layer green sheet 502G can freely shrink (arrows F1 in FIG. 9). By contrast, the third-layer green sheet 503G attempts to shrink, but fails to sufficiently shrink until the paste 505 completely burns off, since the paste 505 hinders shrinkage (arrows F2 in FIG. 9). Therefore, conceivably, the difference between shrinkages F1 and F2 causes stress between the layers, resulting in development of the above-mentioned crack K.

This problem arises also in the case of use of a burning-off sheet in place of the burning-off paste.

SUMMARY OF THE INVENTION

In view of the above problems of the prior art, an object of the present invention is to provide a laminate-type sensor element which has an internal space formed by lamination of ceramic layers and prevents development of a crack between the ceramic layers exposed to the internal space, a gas sensor having the sensor element, and a method for manufacturing the sensor element.

The above object has been achieved by providing, in a first aspect of the present invention, (1) a gas sensor which comprises: a sensor element having a laminate structure, and extending in an axial direction, the gas sensor element comprising: a first ceramic layer and a second ceramic layer disposed apart from each other in a laminating direction; a third ceramic layer intervening between the first ceramic layer and the second ceramic layer in the laminating direction and having a hollow space formed therein; and an internal space which is the hollow space surrounded by the first ceramic layer, the second ceramic layer, and the third ceramic layer. At a periphery of the internal space, a fourth ceramic layer containing as a main component a ceramic material different from a ceramic material contained as a main component in the first ceramic layer and the third ceramic layer intervenes between the first ceramic layer and the third ceramic layer which are exposed to the internal space.

In the case of forming the internal space using a burning-off material in manufacture of the sensor element, the green sheets which are to become the first ceramic layer and the second ceramic layer can freely shrink. By contrast, since the burning-off material is charged into a hollow space of the green sheet which is to become the third ceramic layer, because of hindrance by the burning-off material, the green sheet fails to sufficiently shrink until the burning-off material completely burns off. As a result, since the green sheets adjacent in a direction of lamination differ in shrinkage, stress is applied between the layers, potentially resulting in cracking.

Thus, according to the sensor element (1) above, a paste (or sheet) used to form the fourth ceramic layer intervenes between the green sheets which are to become the first ceramic layer and the third ceramic layer. The fourth-ceramic-layer paste (or sheet) contains as a main component a ceramic material different from the ceramic material contained as a main component in the green sheets so as to start to shrink at a lower temperature (a lower shrinkage-starting temperature) than do the green sheets. As a result, the fourth-ceramic-layer paste (or sheet) shrinks toward the burning-off material and aids shrinkage of the green sheet which is to become the third ceramic layer, thereby mitigating the difference in shrinkage between the adjacent green sheets. Accordingly, application of stress between the first ceramic layer and the third ceramic layer is prevented, whereby cracking can be prevented.

In a preferred embodiment (2) of the gas sensor element (1) above, the fourth ceramic layer has a lower shrinkage-starting temperature than that of the first ceramic layer and the third ceramic layer.

As a result, cracking can be reliably prevented.

In another preferred embodiment (3) of the gas sensor element (1) or (2) above, at the periphery of the internal space, a fifth ceramic layer containing as a main component a ceramic material different from a ceramic material contained as a main component in the second ceramic layer and the third ceramic layer intervenes between the second ceramic layer and the third ceramic layer which are exposed to the internal space.

According to the gas sensor element (3) above, a paste (or sheet) used to form the fifth ceramic layer intervenes between the green sheets which are to become the second ceramic layer and the third ceramic layer. The fifth-ceramic-layer paste (or sheet) contains as a main component a ceramic material different from the ceramic material contained as a main component in the green sheets so as to start to shrink at a lower temperature (a lower shrinkage-starting temperature) than do the green sheets. As a result, the fifth-ceramic-layer paste (or sheet) shrinks toward the burning-off material and aids shrinkage of the green sheet which is to become the third ceramic layer, thereby mitigating the difference in shrinkage between the adjacent green sheets. Accordingly, application of stress between the second ceramic layer and the third ceramic layer is prevented, whereby cracking can be prevented.

In yet another preferred embodiment (4) of the gas sensor element (3) above, the fifth ceramic layer has a lower shrinkage-starting temperature than the second ceramic layer and the third ceramic layer.

As a result, cracking can be reliably prevented.

In yet another preferred embodiment (5) of the gas sensor element of any of (1) to (4) above, the fourth ceramic layer extends across the periphery of the internal space.

According to the gas sensor element (5) above, since a shrinkage force of the fourth-ceramic-layer paste is more reliably transmitted to the green sheet which is to become the third ceramic layer, the effect of preventing cracking is enhanced.

In yet another preferred embodiment (6) of the gas sensor element of any of (1) to (5) above, the fourth ceramic layer is a porous layer.

According to the gas sensor element (6) above, in the case where the fourth ceramic layer is formed on a porous layer, the fourth ceramic layer does not hinder air flow through that porous layer.

In yet another preferred embodiment (7) of the gas sensor element of any of (1) to (6) above, the first ceramic layer and the third ceramic layer contain $Al_2O_3$ in excess of 50 mass %, and the fourth ceramic layer contains $ZrO_2$ in excess of 50 mass %.

According to the gas sensor element (7) above, the shrinkage-starting temperature of the fourth ceramic layer can be reliably lowered.

In yet another preferred embodiment (8) of the gas sensor element of any of (1) to (7) above, the fourth ceramic layer is not exposed at outer surfaces of the first ceramic layer and the third ceramic layer.

If the fourth ceramic layer is exposed at the outer surfaces of the first ceramic layer and the third ceramic layer, the fourth ceramic layer may crack as a result of external water splashing on the fourth ceramic layer or thermal shock imparted to the fourth ceramic layer.

By employing a structure in which the fourth ceramic layer is not exposed at the outer surfaces of the first ceramic layer and the third ceramic layer, cracking can be prevented, which would otherwise result from contact with water or exposure to heat shock.

In yet another preferred embodiment (9) of the gas sensor element of any of (2) to (8) above, the fifth ceramic layer extends across the periphery of the internal space.

According to the gas sensor element (9) above, since a shrinkage force of the fifth-ceramic-layer paste is more reliably transmitted to the green sheet which is to become the third ceramic layer, the effect of preventing cracking is enhanced.

In yet another preferred embodiment (10) of the gas sensor element of any of (2) to (9) above, the fifth ceramic layer is a porous layer.

According to the gas sensor element (10) above, in the case where the fifth ceramic layer is formed on a porous layer, the fifth ceramic layer does not hinder air flow through that porous layer.

In yet another preferred embodiment (11) of the gas sensor element of any of (2) to (10) above, the second ceramic layer and the third ceramic layer contain $Al_2O_3$ in excess of 50 mass %, and the fifth ceramic layer contains $ZrO_2$ in excess of 50 mass %.

According to the gas sensor element (11) above, the shrinkage-starting temperature of the fifth ceramic layer can be reliably lowered.

In yet another preferred embodiment (12) of the gas sensor element of an of 2 to 11 above, the fifth ceramic layer is not exposed at outer surfaces of the second ceramic layer and the third ceramic layer.

If the fifth ceramic layer is exposed at the outer surfaces of the second ceramic layer and the third ceramic layer, the fifth ceramic layer may crack as a result of external water splashing on the fifth ceramic layer or thermal shock imparted to the fifth ceramic layer.

By employing a structure in which the fifth ceramic layer is not exposed at the outer surfaces of the second ceramic layer and the third ceramic layer, cracking can be prevented, which would otherwise result from contact with water or exposure to heat shock.

In a second aspect (13), the present invention (13) provides a sensor including the sensor element of any of (1) to (12) above and a metallic shell which holds the sensor element.

In a third aspect (14), the present invention provides a method for manufacturing a sensor element having a laminate structure, and extending in an axial direction, the method comprising: laminating a third ceramic green sheet having a hollow space formed therein, on a first ceramic green sheet; charging a burning-off material into the hollow space; laminating a second ceramic green sheet on the third ceramic green sheet to form a laminate of the first ceramic green sheet, the third ceramic green sheet, and the second ceramic green sheet; and firing the laminate to burn off the burning-off material, thereby manufacturing the sensor element which includes a first ceramic layer, a second ceramic layer, and a third ceramic layer corresponding to the first, second, and third ceramic green sheets and which includes, as an internal space, the hollow space surrounded by the first ceramic layer, the second ceramic layer, and the third ceramic layer. Before the third ceramic green sheet is laminated on the first ceramic green sheet, at a periphery of the internal space, a fourth paste or sheet that contains a fourth ceramic containing as a main component a ceramic material different from a ceramic material contained as a main component in the first ceramic green sheet and the third ceramic green sheet is disposed in a region between the first ceramic green sheet and the third ceramic green sheet which are in contact with the burning-off material.

In a preferred embodiment (15) of the method (14) for manufacturing a sensor element, the fourth paste or sheet has a lower shrinkage-starting temperature than that of the first ceramic green sheet and the third ceramic green sheet.

In another preferred embodiment (16) of the method (14) for manufacturing a sensor element, at the periphery of the internal space, a fifth paste or sheet that contains a fifth ceramic containing as a main component a ceramic material different from a ceramic material contained as a main component in the second ceramic green sheet and the third ceramic green sheet is disposed between the second ceramic green sheet and the third ceramic green sheet which are in contact with the burning-off material, followed by the firing step.

In yet another preferred embodiment (17) of the method (16) for manufacturing a sensor element, the fifth paste or sheet has a lower shrinkage-starting temperature than that of the second ceramic green sheet and the third ceramic green sheet.

Effect of the Invention

According to the present invention, in a laminate-type sensor element having an internal space defined by laminating ceramic layers, cracking between the ceramic layers exposed to the internal space can be prevented.

DESCRIPTION OF REFERENCE NUMERALS

Figure 1:
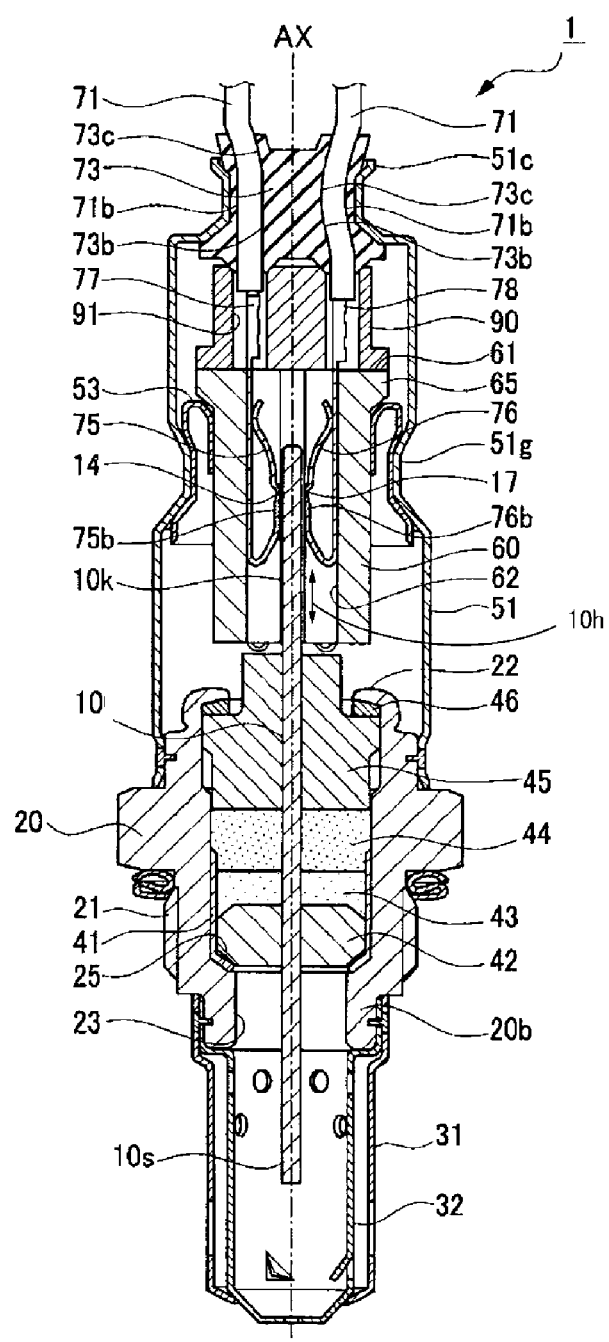
FIG. 1 is a sectional view of a gas sensor ($NO_x$ sensor) according to an embodiment of the present invention, taken along a longitudinal direction thereof.

Reference numerals used to identify various features in the drawings include the following.

1: gas sensor
10: sensor element
10*f*: periphery of an internal space
10G: internal space (hollow space)
150: internal space (first measuring chamber)
10*p*: sheet that contains burning-off material
20: metallic shell
118B: first ceramic layer (third dense layer)
121*s*: first ceramic layer (insulation layer)
115: second ceramic layer (second dense layer)
111*s*: second ceramic layer (insulation layer)
118: third ceramic layer (first dense layer)
140: third ceramic layer (insulator)
181, 182: fourth ceramic layer
191, 192: fifth ceramic layer
118BG: first ceramic green sheet
115G: second ceramic green sheet
118G: third ceramic green sheet
181*p*: fourth paste
191*p*: fifth paste
AX: longitudinal direction (axial line)

DETAILED DESCRIPTION OF THE PREFERRED EMBODIMENTS

An embodiment of the present invention will next be described in greater detail with reference to the drawings. However, the present invention should not be construed as being limited thereto.

Figure 2:
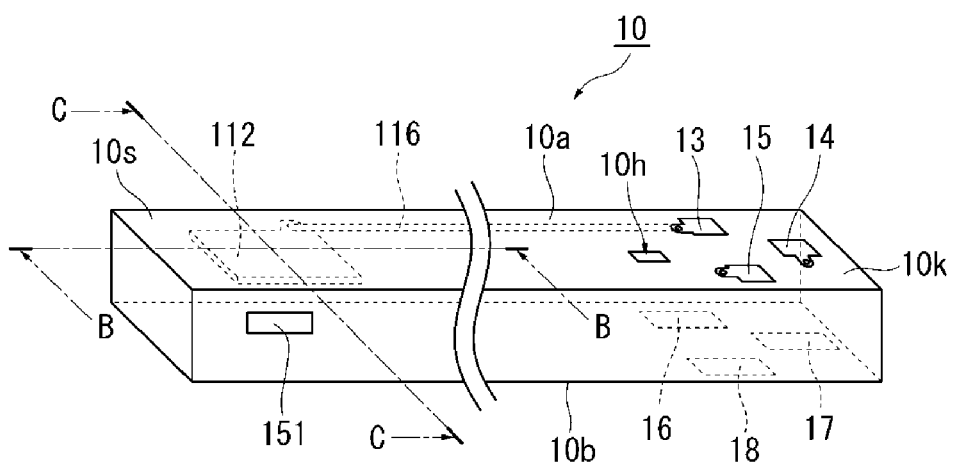
FIG. 2 is a perspective view of the sensor element.
Figure 3:
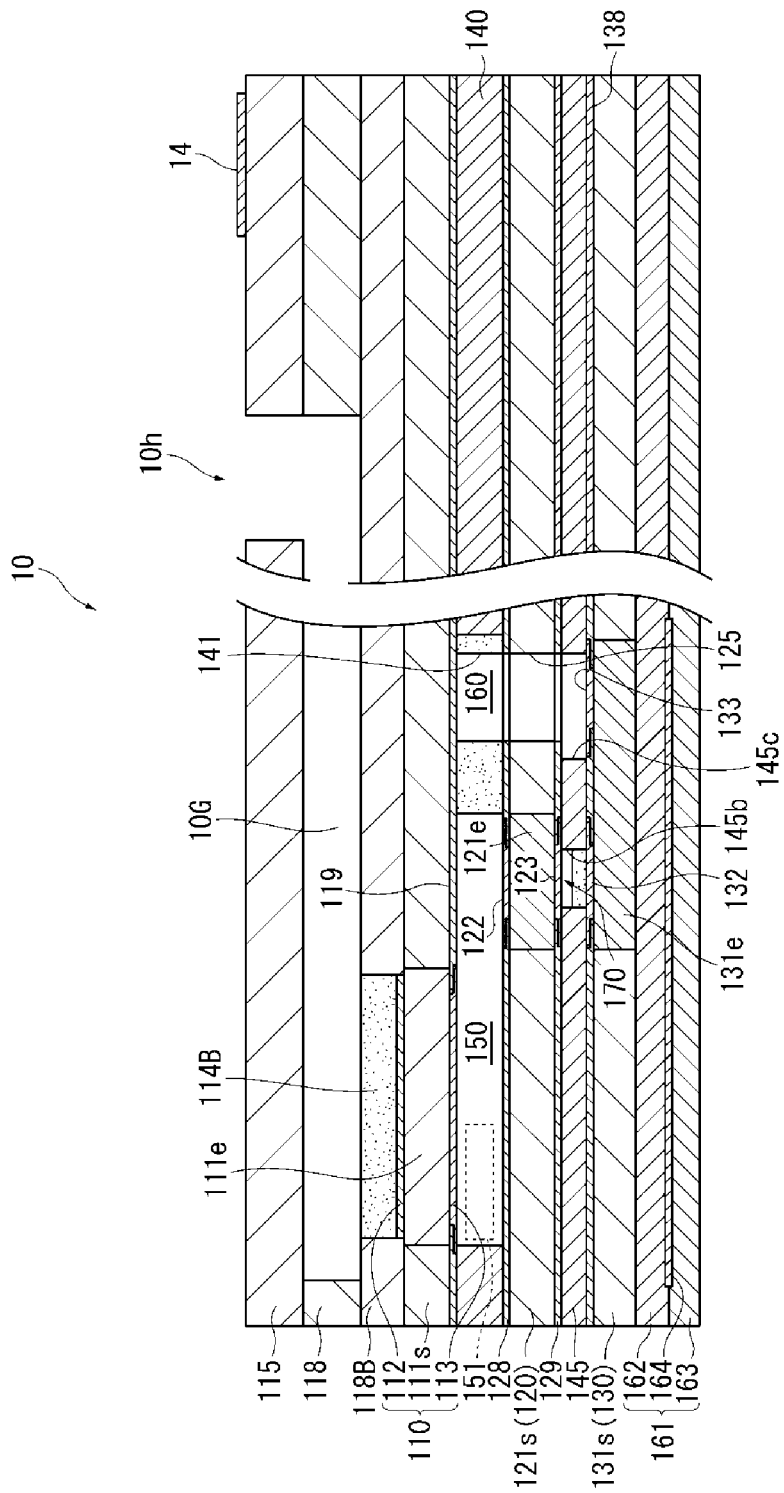
FIG. 3 is a sectional view taken along line B-B of FIG. 2.
Figure 4:
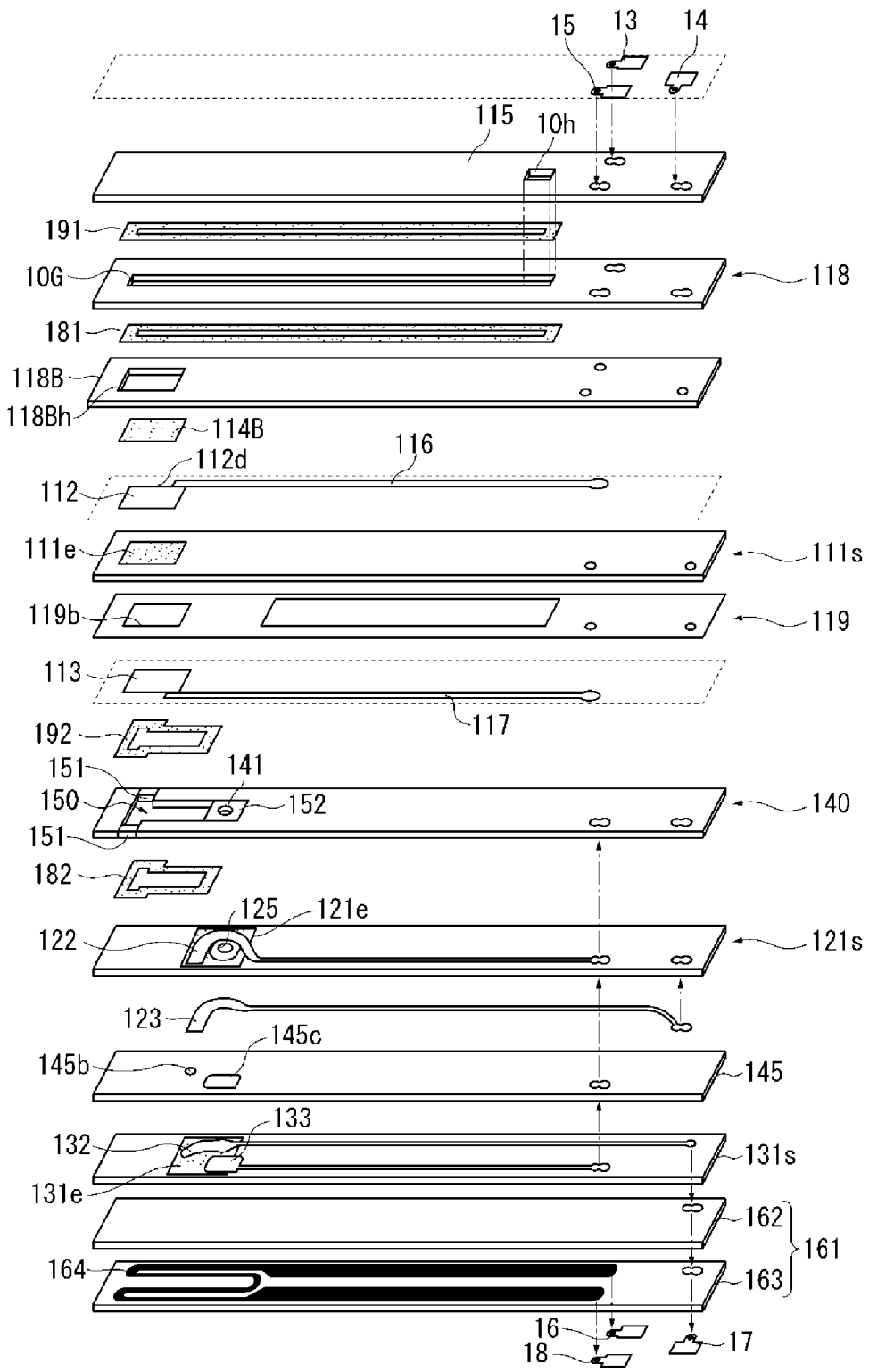
FIG. 4 is an exploded perspective view of the sensor element.
Figure 5:
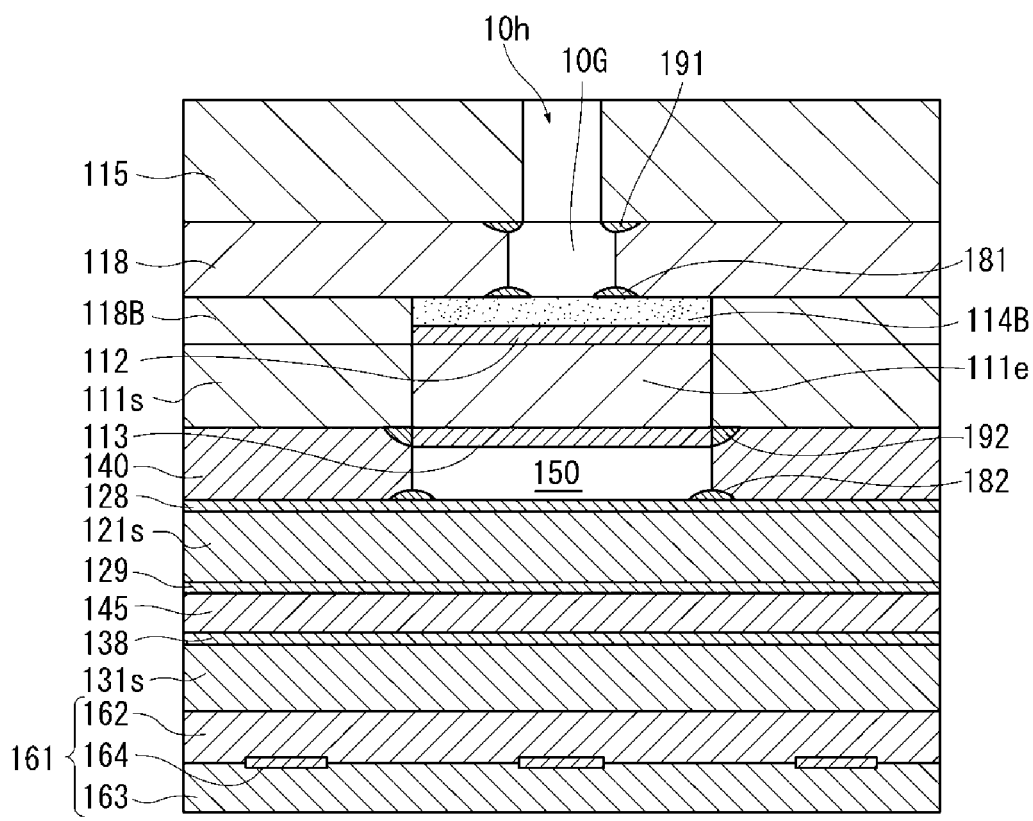
FIG. 5 is a sectional view taken along line C-C of FIG. 2.

FIG. 1 is a longitudinal sectional view (a sectional view cut in a longitudinal direction along an axial line AX) of a gas sensor ($NO_x$ sensor) 1 according to an embodiment of the present invention; FIG. 2 is a perspective view of a sensor element 10; FIG. 3 is a sectional view taken along line B-B (axial line AX) of FIG. 2; FIG. 4 is an exploded perspective view of the sensor element 10; and FIG. 5 is a sectional view taken along line C-C (a line orthogonal to the axial line AX) of FIG. 2.

Notably, a direction along the axial line AX of the sensor element (axial direction) is called the "longitudinal direction" as appropriate. A "width direction" of the sensor element is perpendicular to the "longitudinal direction (axial direction)."

The gas sensor 1 is an $NO_x$ sensor having the sensor element 10 capable of detecting the concentration of a particular gas ($NO_x$) in exhaust gas, which is gas under measurement, and attached, for use, to an exhaust pipe (not shown) of an internal combustion engine. The gas sensor 1 includes a tubular metallic shell 20 having a screw portion 21 formed on an outer surface thereof at a predetermined position and adapted to fix the gas sensor 1 to the exhaust pipe. The sensor element 10 has a narrow, elongated plate shape extending in the direction of the axial line AX and is held in the metallic shell 20.

More specifically, the gas sensor 1 further includes a holding member 60 having an insertion hole 62 into which a rear end portion 10*k* (an upper end portion in FIG. 1) of the sensor element 10 is inserted, and six terminal members held inside the holding member 60. Notably, FIG. 1 shows only two (namely, terminal members 75 and 76) of the six terminal members.

A total of six electrode terminals 13 to 18 (FIG. 1 shows only the electrode terminals 14 and 17), each having a rectangular shape in plan view, are formed on the rear end portion 10*k* of the sensor element 10. The aforementioned terminal members are in elastic contact with and are thus electrically connected to the electrode terminals 13 to 18, respectively. For example, an element contact portion 75*b* of the terminal member 75 is in elastic contact with and is thus electrically connected to the electrode terminal 14. Also, an element contact portion 76*b* of the terminal member 76 is in elastic contact with and is thus electrically connected to the electrode terminal 17.

Further, different lead wires 71 are electrically connected to the six terminal members (terminal members 75, 76, etc.), respectively. For example, as shown in FIG. 1, a lead wire crimp portion 77 of the terminal member 75 is crimped to a core wire of the lead wire 71. Also, a lead wire crimp portion 78 of the terminal member 76 is crimped to a core wire of another lead wire 71.

Also, the sensor element 10 has an atmosphere introduction opening 10$h$ which opens at one of two main surfaces of the rear end portion 10$k$ at a position located forward of the electrode terminals 13 to 15 and rearward of a ceramic sleeve 45, described below (see FIG. 2). The atmosphere introduction opening 10$h$ is disposed within the insertion hole 62 of the holding member 60.

As a result, a reference atmosphere confined within an outer casing 51, described below, is introduced into the sensor element 10 from the atmosphere introduction opening 10$h$.

The metallic shell 20 is a tubular member having a through hole 23 extending therethrough in the direction of the axial line AX. The metallic shell 20 has a ledge 25 protruding radially inward and partially constituting the through hole 23. The metallic shell 20 holds the sensor element 10 in the through hole 23 while allowing a forward end portion 10$s$ of the sensor element 10 to protrude outward (downward in FIG. 1) from a forward end thereof and allowing the rear end portion 10$k$ of the sensor element 10 to protrude outward (upward in FIG. 1) from a rear end thereof.

In the through hole 23 of the metallic shell 20, there are disposed an annular ceramic holder 42, two annularly charged talc rings 43 and 44, and the ceramic sleeve 45. More specifically, the ceramic holder 42, the talc rings 43 and 44, and the ceramic sleeve 45 are stacked in this order from the axially forward side (the lower side in FIG. 1) of the metallic shell 20 to the axially rear side (the upper side in FIG. 1) while radially surrounding the sensor element 10.

A metal cup 41 is disposed between the ceramic holder 42 and the ledge 25 of the metallic shell 20. Also, a crimp ring 46 is disposed between the ceramic sleeve 45 and a crimp portion 22 of the metallic shell 20. The crimp portion 22 of the metallic shell 20 is crimped in such a manner as to press the ceramic sleeve 45 forward through the crimp ring 46.

An outer protector 31 and an inner protector 32 which are made of metal (specifically, stainless steel) and have a plurality of holes are welded to a forward end portion 20$b$ of the metallic shell 20 in such a manner as to cover the forward end portion 10$s$ of the sensor element 10. Meanwhile, the outer casing 51 is welded to a rear end portion of the metallic shell 20. The outer casing 51 has a tubular shape extending in the direction of the axial line AX and surrounds the sensor element 10.

The holding member 60 is a tubular member formed of an electrically insulating material (specifically, alumina) and having the insertion hole 62 extending therethrough in the direction of the axial line AX. The aforementioned six terminal members (terminal members 75, 76, etc.) are disposed within the insertion hole 62 (see FIG. 1). The holding member 60 has a collar portion 65 formed at a rear end portion thereof and protruding radially outward. The holding member 60 is held by an internal support member 53 in such a manner that the collar portion 65 is in contact with the internal support member 53. Notably, the internal support member 53 is held to the outer casing 51 by means of a crimp portion 51$g$ of the outer casing 51 being crimped radially inward.

An insulation member 90 is disposed on a rear end surface 61 of the holding member 60. The insulation member 90 is formed of an electrically insulating material (specifically, alumina) and has a cylindrical shape. The insulation member 90 has six through holes 91 extending therethrough in the direction of the axial line AX. The lead wire crimp portions (lead wire crimp portions 77, 78, etc.) of the aforementioned terminal members are disposed in the through holes 91, respectively.

An elastic seal member 73 formed of fluororubber is disposed radially inward of a rear end opening portion 51$c$ of the outer casing 51 located at an axially rear end portion (an upper end portion in FIG. 1) of the outer casing 51. The elastic seal member 73 has six cylindrical insertion holes 73$c$ extending therethrough in the direction of the axial line AX. The insertion holes 73$c$ are defined by insertion hole surfaces 73$b$ (cylindrical inner wall surfaces), respectively, of the elastic seal member 73. The lead wires 71 are inserted through the insertion holes 73$c$ in one-to-one relation. The lead wires 71 extend to the outside of the gas sensor 1 through the insertion holes 73$c$ of the elastic seal member 73. The elastic seal member 73 is radially deformed in an elastically compressive manner through radially inward crimping of the rear end opening portion 51$c$ of the outer casing 51, whereby the insertion hole surfaces 73$b$ and corresponding outer circumferential surfaces 71$b$ of the lead wires 71 are brought into close contact with one another, thereby establishing a watertight seal between the insertion hole surfaces 73$b$ and the corresponding outer circumferential surfaces 71$b$ of the lead wires 71.

Meanwhile, as shown in FIG. 3, the sensor element 10 includes solid electrolyte bodies 111$e$, 121$e$, and 131$e$ formed respectively in plate-shaped insulation layers 111$s$, 121$s$, and 131$s$, and insulators 140 and 145 disposed between the solid electrolyte bodies 111$e$, 121$e$, and 131$e$, and has a structure in which these members are laminated together in the laminating direction. The sensor element 10 further includes a heater 161 laminated on the back surface of the solid electrolyte body 131$e$. The heater 161 includes plate-shaped insulators 162 and 163 formed primarily of alumina and a heater pattern 164 (formed primarily of Pt) embedded between the insulators 162 and 163.

Notably, the solid electrolyte bodies 111$e$, 121$e$, and 131$e$ have approximately rectangular shapes, respectively, and are formed respectively in rectangular openings provided in forward end portions of the insulation layers 111$s$, 121$s$, and 131$s$. In the present embodiment, the solid electrolyte bodies 111$e$ and 131$e$ are formed by transfer of sheet-shaped members to respectively predetermined positions. However, the material for the solid electrolyte bodies 111$e$ and 131$e$ may be embedded in the respective openings.

The solid electrolyte bodies 111$e$, 121$e$, and 131$e$ are formed of zirconia, which is solid electrolyte, and have oxygen ion conductivity. A porous Ip1 positive electrode 112 is provided on the front surface of the solid electrolyte body 111$e$. A porous Ip1 negative electrode 113 is provided on the back surface of the solid electrolyte body 111$e$. Further, a surface of the Ip1 positive electrode 112 is covered with a porous layer 114B.

An Ip1 positive lead 116 is connected to the Ip1 positive electrode 112 (see FIGS. 2 and 4). An Ip1 negative lead 117 (FIG. 4) is connected to the Ip1 negative electrode 113.

As shown in FIG. 4, a third dense layer 118B is laminated on surfaces of the Ip1 positive electrode 112 and the Ip1 positive lead 116 and has a rectangular opening 118Bh formed in a forward end portion thereof. The porous layer 114B is charged into the opening 118Bh.

As shown in FIG. 4, a gas-impermeable first dense layer 118 formed of alumina or the like and having a hollow space 10G is laminated on the front surface of the third dense layer 118B. The porous layer 114B is partially exposed from the hollow space 10G. Side surfaces of the porous layer 114B are covered with the third dense layer 118B and the hollow space 10G is surrounded by the dense layers 115, 118, and 118B.

The hollow space 10G extends straight from the vicinity of the porous layer 114B to a region where the hollow space 10G communicates with the atmosphere introduction opening 10h. The first dense layer 118 has through holes located rearward of the hollow space 10G for establishing electrical communication with the electrode terminals 13 to 15.

Notably, the atmosphere introduction opening 10h is smaller in dimension in the width direction than the hollow space 10G (see FIG. 5).

Further, a gas-impermeable second dense layer 115 formed of alumina or the like is laminated on the front surface of the first dense layer 118 and closes the hollow space 10G. As a result, the Ip1 positive electrode 112 covered with the porous layer 114B is disposed in the hollow space 10G surrounded by the dense layers 115 and 118, thereby being prevented from coming into contact with the gas under measurement.

The atmosphere introduction opening 10h is a rectangular opening formed in the second dense layer 115 at a position corresponding to the rear end of the hollow space 10G, and the hollow space 10G communicates with the atmosphere introduction opening 10h. The atmosphere introduction opening 10h opens at a position located rearward of first porous bodies 151, described below, and allows introduction of the atmosphere, not an exhaust gas. As a result, the Ip1 positive electrode 112 is exposed through the porous layer 114B to the atmosphere introduced from the atmosphere introduction opening 10h.

The solid electrolyte body 111e and the electrodes 112 and 113 constitute an Ip1 cell (pump cell) 110. The Ip1 cell 110 pumps oxygen (so-called oxygen pumping) in/out between an atmosphere in contact with the electrode 112 (an atmosphere within the hollow space 10G different from the gas under measurement around the sensor element 10) and an atmosphere in contact with the electrode 113 (an atmosphere within a first measuring chamber 150, described below; i.e., the gas under measurement around the sensor element 10) in response to pump current Ip1 flowing between the electrodes 112 and 113.

The solid electrolyte body 121e is disposed in such a manner as to face the solid electrolyte body 111e in the laminating direction with the insulator 140 intervening therebetween. A porous Vs negative electrode 122 is provided on the front surface side (upper surface side in FIG. 2) of the solid electrolyte body 121e. Also, a porous Vs positive electrode 123 is provided on the back surface side (lower surface side in FIG. 2) of the solid electrolyte body 121e.

The first measuring chamber 150, which is an internal space of the sensor element 10, is formed between the solid electrolyte body 111e and the solid electrolyte body 121e. The first measuring chamber 150 is an internal space of the sensor element 10 into which the gas under measurement (exhaust gas) flowing through an exhaust passage is first introduced. The first measuring chamber 150 communicates with the outside of the sensor element 10 through the first porous bodies 151 (diffusion resistor portions) (see FIGS. 2 and 4) having gas permeability and water permeability. The first porous bodies 151 are provided at the lateral sides of the first measuring chamber 150 as partitions between the first measuring chamber 150 and the outside of the sensor element 10. The first porous bodies 151 limit the amount of inflow per unit time (diffusion rate) of exhaust gas into the first measuring chamber 150.

A second porous body 152 is provided on the rear side (right side in FIG. 2) of the first measuring chamber 150 as a partition between the first measuring chamber 150 and a second measuring chamber 160, described below. The second porous body 152 limits the amount of flow per unit time of exhaust gas.

The solid electrolyte body 121e and the electrodes 122 and 123 constitute a Vs cell (detection cell) 120. The Vs cell 120 mainly generates electromotive force in accordance with a difference in partial pressure of oxygen between two atmospheres (an atmosphere within the first measuring chamber 150 in contact with the electrode 122 and an atmosphere within a reference oxygen chamber 170 in contact with the electrode 123) separated by the solid electrolyte body 121e.

The solid electrolyte body 131e is disposed in such a manner as to face the solid electrolyte body 121e in the laminating direction with the insulator 145 sandwiched therebetween. A porous Ip2 positive electrode 132 and a porous Ip2 negative electrode 133 are provided on the front surface side (upper surface side in FIG. 2) of the solid electrolyte body 131e.

The reference oxygen chamber 170, which is an isolated small space, is formed between the Ip2 positive electrode 132 and the Vs positive electrode 123. The reference oxygen chamber 170 is an opening portion 145b formed in the insulator 145. In the reference oxygen chamber 170, a porous body made of ceramic is disposed at a side toward the Ip2 positive electrode 132.

A second measuring chamber 160, which is an internal space of the sensor element, is formed at such a position as to face the Ip2 negative electrode 133 in the laminating direction. The second measuring chamber 160 is composed of an opening portion 145c extending through the insulator 145 in the laminating direction, an opening portion 125 extending through the solid electrolyte body 121e in the laminating direction, and an opening portion 141 extending through the insulator 140 in the laminating direction.

The first measuring chamber 150 and the second measuring chamber 160 communicate with each other through the second porous body 152 having gas permeability and water permeability. Therefore, the second measuring chamber 160 communicates with the outside of the sensor element 10 through the first porous bodies 151, the first measuring chamber 150, and the second porous body 152.

The solid electrolyte body 131e and the electrodes 132 and 133 constitute an Ip2 cell 130 (second pump cell) for detecting $NO_x$ concentration. The Ip2 cell 130 moves oxygen (oxygen ions) formed through decomposition of $NO_x$ in the second measuring chamber 160, to the reference oxygen chamber 170 through the solid electrolyte body 131e. At this time, electric current flows between the electrode 132 and the electrode 133 in accordance with the concentration of $NO_x$ contained in exhaust gas (gas under measurement) introduced into the second measuring chamber 160.

The third dense layer 118B, the second dense layer 115, and the first dense layer 118 correspond respectively to the "first ceramic layer," the "second ceramic layer," and the "third ceramic layer" of the invention. The hollow space 10G associated with the layers 115, 118B, and 118 corresponds to the "internal space" of the invention.

Similarly, the insulation layer 121s, the insulation layer 111s, and the insulator 140 correspond respectively to the "first ceramic layer," the "second ceramic layer," and the "third ceramic layer" of the invention. The first measuring chamber 150 associated with the layers 111s, 121s, and 140 corresponds to the "internal space" of the invention.

Next, referring to FIGS. 4 and 5, structural features of the present invention will be described.

As shown in FIGS. 4 and 5, at the periphery of the hollow space 10G, which is an internal space, a fourth ceramic layer 181 intervenes between the third dense layer 118B and the first dense layer 118 which are exposed to the hollow space 10G. Also, a fifth ceramic layer 191 intervenes between the second dense layer 115 and the first dense layer 118 which are exposed to the hollow space 10G.

Similarly, at the periphery of the first measuring chamber 150, which is an internal space, a fourth ceramic layer 182 intervenes between the insulation layer 121s and the insulator 140 which are exposed to the first measuring chamber 150. Also, a fifth ceramic layer 192 intervenes between the insulation layer 111s and the insulator 140 which are exposed to the first measuring chamber 150.

Figure 6:
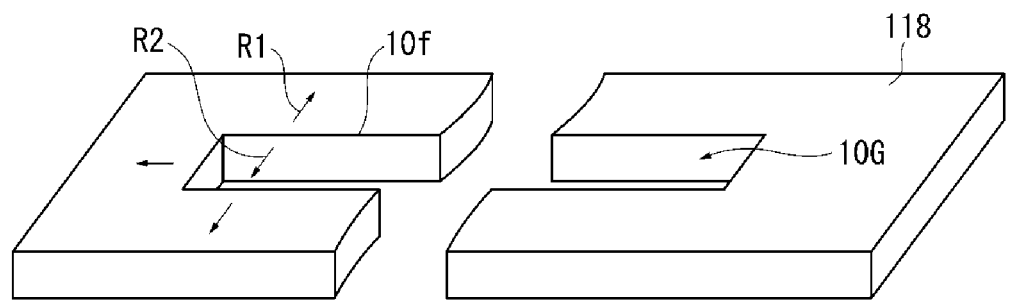
FIG. 6 is a view showing the periphery of an internal space.

Notably, as shown in FIG. 6, "at the periphery of the internal space" means, for example, one of a region R1 which includes the periphery 10f of the hollow space 10G forming the internal space and extends outward from the periphery 10f and a region R2 which includes the periphery 10f and extends inward from the periphery 10f, or both the regions R1 and R2.

In the present embodiment, the fourth ceramic layer 181 and the fifth ceramic layer 191 extend across the periphery of the hollow space 10G in the width direction and the direction of the axial line AX of the sensor element 10.

The fourth ceramic layer 182 extends across the periphery of the first measuring chamber 150 in the width direction and the direction of the axial line AX of the center element 10. The fifth ceramic layer 192 is formed in a region including the periphery of the first measuring chamber 150 and extending outward from the periphery of the first measuring chamber 150.

The fourth ceramic layer 181 contains as a main component a ceramic material different from a ceramic material contained as a main component in the third dense layer 118B and the first dense layer 118 which are in contact with the fourth ceramic layer 181. The fifth ceramic layer 191 contains as a main component a ceramic material different from a ceramic material contained as a main component in the second dense layer 115 and the first dense layer 118 which are in contact with the fifth ceramic layer 191.

Similarly, the fourth ceramic layer 182 contains as a main component a ceramic material different from a ceramic material contained as a main component in the insulation layer 121s and the insulator 140 which are in contact with the fourth ceramic layer 182. The fifth ceramic layer 192 contains as a main component a ceramic material different from a ceramic material contained as a main component in the insulation layer 111s and the insulator 140 which are in contact with the fifth ceramic layer 192.

As described above, cracking between the ceramic layers 115, 118, and 118B can be prevented in the case where the fourth ceramic layer 181 is formed by using, as a main component, a ceramic material different from the ceramic material contained as a main component in the third dense layer 118B and the first dense layer 118. Also, the fifth ceramic layer 191 is formed by using, as a main component, a ceramic material different from the ceramic material contained as a main component in the second dense layer 115 and the first dense layer 118, so that shrinkage of the fourth ceramic layer 181 and the fifth ceramic layer 191 starts at a lower temperature (a lower shrinkage-starting temperature).

Figure 7:
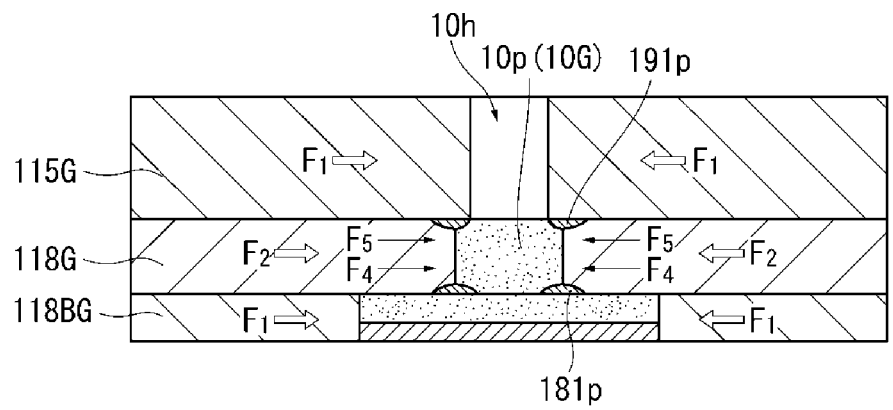
FIG. 7 is a view showing a method for forming the internal space by use of a burning-off paste in manufacture of the sensor element.
Figure 8:
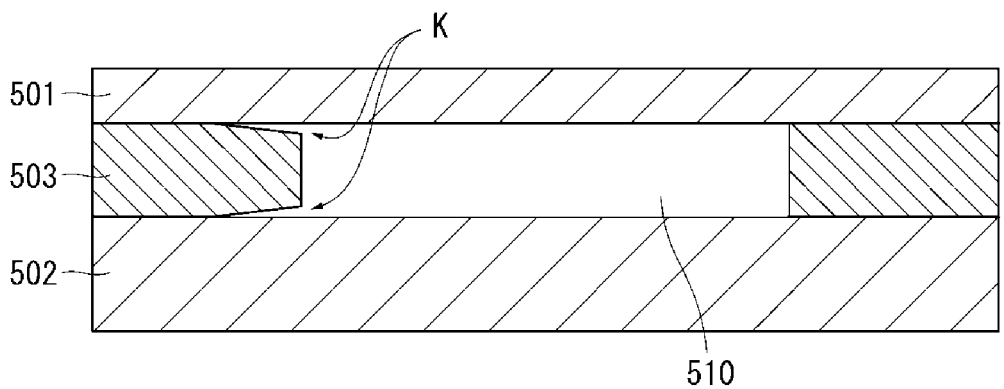
FIG. 8 is a sectional view of a conventional sensor element having an atmosphere introduction hole, taken along a width direction thereof.
Figure 9:
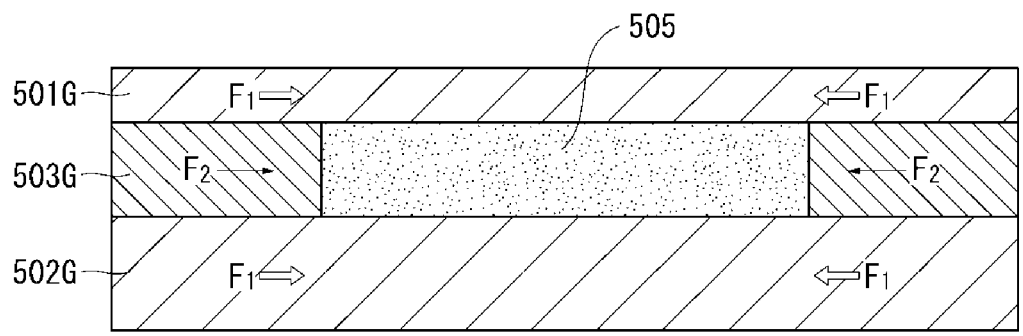
FIG. 9 is a view showing a cracking mechanism in the case of forming the atmosphere introduction hole using a burning-off paste in manufacture of the sensor element of FIG. 8.

As shown in FIG. 7, the hollow space 10G is formed in the following manner. A first-dense-layer green sheet 118G is laminated on a third-dense-layer green sheet 118BG. Further, a sheet 10p that contains burning-off particles (carbon or the like) is charged into a hollow space of the first-dense-layer green sheet 118G which is to become the hollow space 10G. Subsequently, a second-dense-layer green sheet 115G is laminated on the first-dense-layer green sheet 118G. The resulting laminate is subjected to firing, whereby the sheet 10p burns off to form the hollow space 10G.

In this firing process, the third-dense-layer green sheet 118BG and the second-dense-layer green sheet 115G can freely shrink (arrows F1 in FIG. 7). By contrast, the first-dense-layer green sheet 118G attempts to shrink, but fails to sufficiently shrink until the sheet 10p burns off completely, since the sheet 10p hinders the shrinkage (arrows F2 in FIG. 7).

In the present embodiment, a fourth-ceramic-layer paste 181p intervenes between the third-dense-layer green sheet 118BG and the first-dense-layer green sheet 118G. The fourth-ceramic-layer paste 181p contains as a main component a ceramic material different from a ceramic material contained as a main component in the third-dense-layer green sheet 118BG and the first-dense-layer green sheet 118G so as to start to shrink at a lower temperature (a lower shrinkage-starting temperature) than do the green sheets. As a result, the fourth-ceramic-layer paste 181p shrinks toward the sheet 10p and aids shrinkage of the first-dense-layer green sheet 118G, thereby mitigating the difference in shrinkage between F1 and F2. Accordingly, application of stress between the layer green sheets 118BG and 118G is prevented, whereby cracking can be prevented.

Similarly, a fifth-ceramic-layer paste 191p intervenes between the second-dense-layer green sheet 115G and the first-dense-layer green sheet 118G. The fifth-ceramic-layer paste 191p contains as a main component a ceramic material different from a ceramic material contained as a main component in the second-dense-layer green sheet 115G and the first-dense-layer green sheet 118G so as to start to shrink at a lower temperature (a lower shrinkage-starting temperature) than do the green sheets. As a result, the fifth-ceramic-layer paste 191p shrinks toward the sheet 10p and aids shrinkage of the first-dense-layer green sheet 118G, thereby mitigating the difference in shrinkage between F1 and F2. Accordingly, application of stress between the layer green sheets 115G and 118G is prevented, whereby cracking can be prevented.

Since the case of the fourth ceramic layer 182 and the fifth ceramic layer 192 associated with the first measuring chamber 150 is similar to the above case, description thereof is omitted.

The shrinkage-starting temperature is obtained as follows. Green sheets having the same compositions as those of the ceramic layers are prepared. The temperature of each green sheet is increased in the atmosphere so as to progress firing, thereby forming each ceramic layer. The shrinkage-starting temperature is a temperature at which the shrinkage factor becomes 1.05. The shrinkage factor is also called the firing shrinkage ratio and is calculated from the longitudinal or lateral dimension of a green sheet before firing, with the longitudinal or lateral dimension of a corresponding ceramic layer after firing taken as 1.

That is, the shrinkage factor=(the longitudinal or lateral dimension of a green sheet before firing)/(the corresponding dimension of a corresponding ceramic layer after firing).

Alumina can be used to form the first ceramic layer to the third ceramic layer; namely, the layers 115, 118B, 118, 111s, 121s, and 140. The first ceramic layer to the third ceramic layer may not have the same composition. However, preferably, the first ceramic layer to the third ceramic layer have generally the same composition, since members of the sensor element become uniform in characteristics such as strength.

The fourth ceramic layer and the fifth ceramic layer may contain, for example, $ZrO_2$ in excess of 50 mass % and the composition (alumina) of the first ceramic layer to the third ceramic layer as the balance. A $ZrO_2$ content in excess of 50 mass % can reliably lower the shrinkage-starting temperature.

According to an example composition of the first ceramic layer to the third ceramic layer, the $ZrO_2$ content is lower than that of the fourth ceramic layer and the fifth ceramic layer (e.g., the $Al_2O_3$ content is in excess of 50 mass %, and the $ZrO_2$ content is less than 50 mass %).

Specifically, for example, the first ceramic layer to the third ceramic layer contain alumina in an amount of 98 mass % and $ZrO_2$ in an amount of 2 mass %, whereas the fourth ceramic layer and the fifth ceramic layer contain $ZrO_2$ in an amount of 80 mass % and alumina in an amount of 20 mass %.

As shown in FIG. 5, when at least one of the fourth ceramic layer 181 and the fifth ceramic layer 191 extends across the periphery of the hollow space 10G, since the shrinkage force of the fourth-ceramic-layer paste 181p and the fifth-ceramic-layer paste 191p shown in FIG. 7 is more reliably transmitted to the first-dense-layer green sheet 118G, the effect of preventing cracking is enhanced.

The expression "extends across the periphery" means to extend across the periphery at least in one of the width direction and the direction of the axial line AX of the sensor element 10; however, extension across the periphery in both directions is preferred.

In the case of the fifth ceramic layer 192 shown in FIG. 5, since the Ip1 negative electrode 113 is disposed inwardly of the periphery of the first measuring chamber 150, in order to not hinder the function of the Ip1 negative electrode 113, the fifth ceramic layer 192 is formed outwardly of the periphery of the first measuring chamber 150.

Instead of forming the fifth ceramic layer 192 outwardly of the periphery of the first measuring chamber 150, the fifth ceramic layer 192 may be formed in such a manner as to extend across the periphery of the first measuring chamber 150 such that the fifth ceramic layer 192 is separated from the Ip1 negative electrode 113 (or a gap is formed between the fifth ceramic layer 192 and the Ip1 negative electrode 113) in a region located inwardly of the periphery of the first measuring chamber 150.

The fourth ceramic layer 181 shown in FIG. 5 is formed on the front surface of the porous layer 114B. In such a case, in order to not hinder air flow through the porous layer 114B, the fourth ceramic layer 181 is preferably a porous layer.

In order to form the fourth ceramic layer 181 as a porous layer, burning-off particles (carbon or the like) may be contained in a paste used to form the fourth ceramic layer 181.

If the fourth ceramic layer 181 is exposed at the outer surfaces of the second dense layer 115 and the first dense layer 118, the fourth ceramic layer 181 may crack as a result of splashing of external water on the fourth ceramic layer 181 or thermal shock imparted to the fourth ceramic layer 181.

Thus, as shown in FIG. 5, preferably, the fourth ceramic layer 181 is not exposed at the outer surfaces of the second dense layer 115 and the first dense layer 118.

The same also applies to the fourth ceramic layer 182 and the fifth ceramic layers 191 and 192.

Detection of $NO_x$ concentration by the gas sensor 1 of the present embodiment will now be described briefly.

As the heater pattern 164 rises in temperature, the solid electrolyte bodies 111e, 121e, and 131e of the sensor element 10 are heated and activated. As a result, the Ip1 cell 110, the Vs cell 120, and the Ip2 cell 130 start their operations.

Exhaust gas which flows through an exhaust passage (not shown) is introduced into the first measuring chamber 150 while being limited in flow rate by the first porous bodies 151. At this time, in the Vs cell 120, a weak current Icp is caused to flow from the electrode 123 to the electrode 122. As a result, oxygen contained in exhaust gas can receive electrons from the electrode 122, which is a negative electrode, within the first measuring chamber 150 and becomes oxygen ions. The oxygen ions flow through the solid electrolyte body 121e and move into the reference oxygen chamber 170. That is, as a result of flow of the current Icp between the electrodes 122 and 123, oxygen in the first measuring chamber 150 is sent to the reference oxygen chamber 170.

In the case where the oxygen concentration of exhaust gas introduced into the first measuring chamber 150 is lower than a predetermined value, the current Ip1 is caused to flow through the Ip1 cell 110 in such a manner that the electrode 112 becomes a negative electrode, so as to pump oxygen into the first measuring chamber 150 from the outside of the sensor element 10. By contrast, in the case where the oxygen concentration of exhaust gas introduced into the first measuring chamber 150 is higher than the predetermined value, the current Ip1 is caused to flow through the Ip1 cell 110 in such a manner that the electrode 113 becomes a negative electrode, so as to pump out oxygen from inside the first measuring chamber 150 to the outside of the sensor element 10.

Exhaust gas whose oxygen concentration has been adjusted in the first measuring chamber 150 as mentioned above is introduced into the second measuring chamber 160 through the second porous body 152. $NO_x$ contained in exhaust gas comes into contact with the electrode 133 within the second measuring chamber 160 and is decomposed (reduced) on the electrode 133 into nitrogen and oxygen through application of the voltage Vp2 between the electrodes 132 and 133. Oxygen generated through the decomposition flows, in the form of oxygen ions, through the solid electrolyte body 131e and moves into the reference oxygen chamber 170. At this time, residual oxygen which has not been pumped out from the first measuring chamber 150 similarly moves into the reference oxygen chamber 170 through operation of the Ip2 cell 130. Thus, current stemming from $NO_x$ and current stemming from the residual oxygen flow through the Ip2 cell 130. Notably, oxygen which has moved into the reference oxygen chamber 170 is discharged to the outside (the atmosphere) through the Vs positive electrode 123 exposed to the reference oxygen chamber 170, and the Vs positive lead and through the Ip2 positive electrode 132 and the Ip2 positive lead; accordingly, the Vs positive lead and the Ip2 positive lead are porous.

Since the residual oxygen which has not been pumped out from the first measuring chamber 150 is adjusted in concentration to the predetermined value as mentioned above, current stemming from the residual oxygen can be considered generally constant and thus has little influence on variation in current stemming from $NO_x$; thus, current flowing through the Ip2 cell 130 is proportional to $NO_x$ concentration. Therefore, by means of detecting the current Ip2 which flows through the Ip2 cell 130, the concentration of $NO_x$ in exhaust gas can be detected based on the detected current Ip2.

In the present embodiment, an alumina insulation layer 119 is formed on the back surface of the insulation layer 111s, excluding a region corresponding to the Ip1 negative electrode 113. The Ip1 negative electrode 113 is in contact with the solid electrolyte body 111e through a through hole 119b (see FIG. 4) extending through the alumina insulation layer 119 in the laminating direction.

Further, in the present embodiment, an alumina insulation layer 128 is formed on the front surface of the insulation layer 121s, excluding a region corresponding to the Vs negative electrode 122. The Vs negative electrode 122 is in contact with the solid electrolyte body 121e through a through hole (not shown) extending through the alumina insulation layer 128 in the laminating direction.

Further, an alumina insulation layer 129 is formed on the back surface of the insulation layer 121s, excluding a region corresponding to the Vs positive electrode 123. The Vs positive electrode 123 is in contact with the solid electrolyte body 121e through a through hole (not shown) extending through the alumina insulation layer 129 in the laminating direction.

Further, in the present embodiment, an alumina insulation layer 138 is formed on the front surface of the insulation layer 131s, excluding a region corresponding to the Ip2 positive electrode 132. The Ip2 positive electrode 132 is in contact with the solid electrolyte body 131e through a through hole (not shown) extending through the alumina insulation layer 138 in the laminating direction. Further, the alumina insulation layer 138 is formed on the front surface of the insulation layer 131s also, excluding a region corresponding to the Ip2 negative electrode 133. The Ip2 negative electrode 133 is in contact with the solid electrolyte body 131e through a through hole (not shown) extending through the alumina insulation layer 138 in the laminating direction.

Next, a method for manufacturing a sensor element according to an embodiment of the present invention will be described.

As shown in FIG. 7, according to the method for manufacturing a sensor element according to the embodiment of the present invention, a third ceramic green sheet (the first-dense-layer green sheet 118G) having a hollow space formed therein by press working or the like is prepared. A sheet 10p that contains a burning-off material is embedded in the hollow space of the third ceramic green sheet. The resultant third ceramic green sheet is laminated on the front surface of a first ceramic green sheet (the third-dense-layer green sheet 118BG). A second ceramic green sheet (the second-dense-layer green sheet 115G) is laminated on the front surface of the third ceramic green sheet. The resultant laminate is subjected to firing, whereby the sheet 10P burns off to form the hollow space 10G surrounded by the first ceramic layer, the second ceramic layer, and the third ceramic layer. As a result, the laminate-type sensor element 10 extending in the direction of the axial line AX and having the hollow space 10G as an internal space is obtained.

At the periphery of the hollow space 10G, the fourth paste 181p that contains a fourth ceramic containing as a main component a ceramic material different from a ceramic material contained as a main component in the first ceramic green sheet and the third ceramic green sheet is applied between the first ceramic green sheet and the third ceramic green sheet which are in contact with the sheet 10p, followed by firing.

By selecting such a fourth paste 181p that starts to shrink at a lower temperature (a lower shrinkage-starting temperature) than do the first ceramic green sheet and the third ceramic green sheet, cracking can be prevented as mentioned above.

In the method for manufacturing a sensor element according to the embodiment of the present invention, at the periphery of the hollow space 10G, the fifth paste 191p that contains a fifth ceramic containing as a main component a ceramic material different from a ceramic material contained as a main component in the second ceramic green sheet and the third ceramic green sheet may further be applied between the second ceramic green sheet and the third ceramic green sheet which are in contact with the sheet 10p, followed by firing. In this case, firing is performed after applying the fourth paste 181p and the fifth paste 191p.

By selecting such a fifth paste 191p that starts to shrink at a lower temperature (a lower shrinkage-starting temperature) than do the second ceramic green sheet and the third ceramic green sheet, cracking can be prevented as mentioned above.

The present invention is not limited to the above embodiments, and encompasses various modifications and equivalents which fall within the spirit and scope of the invention.

A hollow space is sufficient as the internal space of the sensor element, and examples of the internal space include an atmosphere introduction hole and various measuring chambers. The shape of the internal space is not particularly limited.

The burning-off material may assume the form of a paste in addition to the form of a sheet.

The present invention can be applied to a sensor element (a gas sensor) having at least a detection cell (one or more cells) and thus can be applied to the $NO_x$ sensor element ($NO_x$ sensor) of the present embodiment. However, the present invention is not limited thereto, and the invention encompasses various modifications and equivalents which fall within the spirit and scope of the invention. For example, the present invention may be applied to an oxygen sensor (oxygen sensor element) for detecting the oxygen concentration of a gas under measurement, an HC sensor (HC sensor element) for detecting the HC concentration of gas under measurement, etc.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2019-169124 filed Sep. 18, 2019 and Japanese Patent Application No. 2020-036511 filed Mar. 4, 2020, the above noted applications incorporated herein by reference in their entirety.

What is claimed is:

1. A sensor element having a laminate structure, and extending in an axial direction, the sensor element comprising:
- a first ceramic layer and a second ceramic layer disposed apart from each other in a laminating direction;
- a third ceramic layer intervening between the first ceramic layer and the second ceramic layer in the laminating direction and having a hollow space formed therein; and
- an internal space which is the hollow space surrounded by the first ceramic layer, the second ceramic layer, and the third ceramic layer,
- wherein, at a periphery of the internal space, a fourth ceramic layer containing as a main component a ceramic material different from a ceramic material contained as a main component in the first ceramic layer and the third ceramic layer intervenes between the first ceramic layer and the third ceramic layer which are exposed to the internal space,
- wherein the fourth ceramic layer is a porous layer and has air permeability, and
- wherein, at the periphery of the internal space, a fifth ceramic layer containing as a main component a ceramic material different from the ceramic material contained as the main component in the second ceramic layer and the third ceramic layer intervenes between the second ceramic layer and the third ceramic layer exposed to the internal space.

2. The sensor element as claimed in claim 1, wherein the fourth ceramic layer has a lower shrinkage-starting temperature than that of the first ceramic layer and the third ceramic layer.

3. The sensor element as claimed in claim 1, wherein the fifth ceramic layer has a lower shrinkage-starting temperature than that of the second ceramic layer and the third ceramic layer.

4. The sensor element as claimed in claim 1, wherein the fourth ceramic layer extends across the periphery of the internal space.

5. The sensor element as claimed in claim 1, wherein the first ceramic layer and the third ceramic layer contain $Al_2O_3$ excess of 50 mass %, and the fourth ceramic layer contains $ZrO_2$ in excess of 50 mass %.

6. The sensor element as claimed in claim 1, wherein the fourth ceramic layer is not exposed at outer surfaces of the first ceramic layer and the third ceramic layer.

7. The sensor element as claimed in claim 1, wherein the fifth ceramic layer extends across the periphery of the internal space.

8. The sensor element as claimed in claim 1, wherein the fifth ceramic layer is a porous layer.

9. The sensor element as claimed in claim 1, wherein the second ceramic layer and the third ceramic layer contain $Al_2O_3$ in excess of 50 mass %, and the fifth ceramic layer contains $ZrO_2$ in excess of 50 mass %.

10. The sensor element as claimed in claim 1, wherein the fifth ceramic layer is not exposed at outer surfaces of the second ceramic layer and the third ceramic layer.

11. The sensor element as claimed in claim 1, wherein the fifth ceramic layer is a porous layer and has air permeability.

12. A gas sensor comprising the sensor element as claimed in claim 1 and a metallic shell which holds the sensor element.

13. A sensor element having a laminate structure, and extending in an axial direction, the sensor element comprising:
- a first ceramic layer and a second ceramic layer disposed apart from each other in a laminating direction;
- a third ceramic layer intervening between the first ceramic layer and the second ceramic layer in the laminating direction and having a hollow space formed therein; and
- an internal space which is the hollow space surrounded by the first ceramic layer, the second ceramic layer, and the third ceramic layer,
- wherein, at a periphery of the internal space, a fourth ceramic layer containing as a main component a ceramic material different from a ceramic material contained as a main component in the first ceramic layer and the third ceramic layer intervenes between the first ceramic layer and the third ceramic layer which are exposed to the internal space,
- wherein, at the periphery of the internal space, a fifth ceramic layer containing as a main component a ceramic material different from a ceramic material contained as a main component in the second ceramic layer and the third ceramic layer intervenes between the second ceramic layer and the third ceramic layer exposed to the internal space, and
- wherein the fifth ceramic layer is a porous layer and has air permeability.

14. A method for manufacturing the sensor element having the laminate structure as claimed in claim 1, and extending in the axial direction, the method comprising:
- laminating a third ceramic green sheet having the hollow space formed therein, on a first ceramic green sheet;
- charging a burning-off material into the hollow space;
- laminating a second ceramic green sheet on the third ceramic green sheet to form a laminate of the first ceramic green sheet, the third ceramic green sheet, and the second ceramic green sheet; and
- firing the laminate to burn off the burning-off material, thereby manufacturing the sensor element which includes the first ceramic layer, the second ceramic layer, and the third ceramic layer corresponding to the first, second, and third ceramic green sheets and which includes, as the internal space, the hollow space surrounded by the first ceramic layer, the second ceramic layer, and the third ceramic layer;
- wherein before the third ceramic green sheet is laminated on the first ceramic green sheet, at a periphery of the internal space, a fourth paste or sheet that contains a fourth ceramic containing as a main component a ceramic material different from a ceramic material contained as a main component in the first ceramic green sheet and the third ceramic green sheet is disposed in a region between the first ceramic green sheet and the third ceramic green sheet which are in contact with the burning-off material,
- wherein firing the fourth paste or sheet forms the fourth ceramic layer,
- wherein the fourth ceramic layer is porous and has air permeability,
- wherein, at the periphery of the internal space, a fifth paste or sheet that contains a fifth ceramic containing as a main component a ceramic material different from the ceramic material contained as the main component in the second ceramic green sheet and the third ceramic green sheet is disposed between the second ceramic green sheet and the third ceramic green sheet which are in contact with the burning-off material, followed by the firing step, and wherein firing the fifth paste or sheet forms the fifth ceramic layer.

15. The method for manufacturing the sensor element as claimed in claim 14, wherein the fourth paste or sheet has a lower shrinkage-starting temperature than that of the first ceramic green sheet and the third ceramic green sheet.

16. The method for manufacturing the sensor element as claimed in claim 14, wherein the fifth paste or sheet has a lower shrinkage-starting temperature than that of the second ceramic green sheet and the third ceramic green sheet.

* * * * *